US010828067B2

(12) United States Patent
Katrana et al.

(10) Patent No.: US 10,828,067 B2
(45) Date of Patent: Nov. 10, 2020

(54) COMPRESSIVE DISTAL HUMERUS PLATING SYSTEM

(71) Applicant: Biomet Manufacturing, LLC, Warsaw, IN (US)

(72) Inventors: Nicholas J. Katrana, Fort Wayne, IN (US); Benjamin P. Heilman, Warsaw, IN (US); Thomas M. Vanasse, South Bend, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 709 days.

(21) Appl. No.: 15/137,246

(22) Filed: Apr. 25, 2016

(65) Prior Publication Data

US 2016/0235445 A1    Aug. 18, 2016

Related U.S. Application Data

(63) Continuation of application No. 13/648,302, filed on Oct. 10, 2012, now Pat. No. 9,320,553.
(Continued)

(51) Int. Cl.
*A61B 17/68* (2006.01)
*A61B 17/86* (2006.01)
*A61B 17/80* (2006.01)

(52) U.S. Cl.
CPC ........ *A61B 17/683* (2013.01); *A61B 17/8014* (2013.01); *A61B 17/8042* (2013.01);
(Continued)

(58) Field of Classification Search
CPC . A61B 17/80; A61B 17/8004; A61B 17/8009; A61B 17/8014; A61B 17/8052;
(Continued)

(56) References Cited

U.S. PATENT DOCUMENTS 3,900,025 A     8/1975  Barnes, Jr.
6,302,887 B1   10/2001  Spranza et al.
(Continued)

FOREIGN PATENT DOCUMENTS

WO    WO-2009100520 A1    8/2009
WO    WO-2011049471 A1    4/2011
WO    WO-2013059035 A1    4/2013

OTHER PUBLICATIONS

"U.S. Appl. No. 13/648,302, Advisory Action dated Nov. 3, 2015", 3 pgs.
(Continued)

*Primary Examiner* — Anu Ramana
(74) *Attorney, Agent, or Firm* — Schwegman Lundberg & Woessner, P.A.

(57) ABSTRACT

A system for compressing a fracture can include a first bone plate having a first proximal end and a first distal end, and a second bone plate having a second proximal end and a second distal end. The second bone plate can be spaced apart from the first bone plate. The system can include an expansion member coupled to the second proximal end of the second bone plate. The movement of the expansion member relative to the second bone plate can cause the first distal end of the first bone plate and the second distal end of the second bone plate to move toward each other to compress the fracture.

5 Claims, 9 Drawing Sheets

Related U.S. Application Data

(60) Provisional application No. 61/548,444, filed on Oct. 18, 2011.

(52) U.S. Cl.
CPC ...... *A61B 17/8047* (2013.01); *A61B 17/8057* (2013.01); *A61B 17/8061* (2013.01); *A61B 17/8625* (2013.01); *A61B 17/8685* (2013.01); *A61B 2017/681* (2013.01)

(58) Field of Classification Search
CPC .............. A61B 17/8061; A61B 17/809; A61B 17/1725; A61B 17/7225; A61B 17/7233; A61B 17/725; A61B 17/746
See application file for complete search history.

(56) References Cited

U.S. PATENT DOCUMENTS

| | | | |
|---|---|---|---|
| 6,908,469 | B2 | 6/2005 | Sellers et al. |
| 7,563,263 | B2 | 7/2009 | Orbay et al. |
| 9,320,553 | B2 | 4/2016 | Katrana et al. |
| 2003/0135212 | A1 | 7/2003 | Chow |
| 2003/0135216 | A1* | 7/2003 | Sevrain .............. A61B 17/7059 606/305 |
| 2006/0264949 | A1 | 11/2006 | Kohut et al. |
| 2009/0118768 | A1 | 5/2009 | Sixto, Jr. et al. |
| 2013/0096559 | A1 | 4/2013 | Katrana et al. |

OTHER PUBLICATIONS

"U.S. Appl. No. 13/648,302, Final Office Action dated Aug. 27, 2015", 8 pgs.
"U.S. Appl. No. 13/648,302, Final Office Action dated Dec. 31, 2014", 5 pgs.
"U.S. Appl. No. 13/648,302, Non Final Office Action dated Mar. 6, 2015", 10 pgs.
"U.S. Appl. No. 13/648,302, Non Final Office Action dated Sep. 22, 2014", 7 pgs.
"U.S. Appl. No. 13/648,302, Notice of Allowance dated Dec. 18, 2015", 5 pgs.
"U.S. Appl. No. 13/648,302, Response filed Feb. 12, 2015 to Final Office Action dated Dec. 31, 2014", 12 pgs.
"U.S. Appl. No. 13/648,302, Response filed Aug. 6, 2015 to Non Final Office Action dated Mar. 6, 2015", 14 pgs.
"U.S. Appl. No. 13/648,302, Response filed Aug. 11, 2014 to Restriction Requirement dated Jun. 11, 2014", 3 pgs.
"U.S. Appl. No. 13/648,302, Response filed Oct. 13, 2014 to Non Final Office Action dated Sep. 22, 2014", 14 pgs.
"U.S. Appl. No. 13/648,302, Response filed Oct. 27, 2015 to Final Office Action dated Aug. 27, 2015", 13 pgs.
"U.S. Appl. No. 13/648,302, Response filed Dec. 8, 2015 to Advisory Action dated Nov. 3, 2015 and Final Office Action dated Aug. 27, 2015", 7 pgs.
"U.S. Appl. No. 13/648,302, Restriction Requirement dated Jun. 11, 2014", 5 pgs.
"European Application Serial No. 12778185.4, Office Action dated Aug. 26, 2014", 2 pgs.
"European Application Serial No. 12778185.4, Response filed Feb. 18, 2015 to Office Action dated Aug. 26, 2014", 13 pgs.
"International Application Serial No. PCT/US2012/059426, International Preliminary Report on Patentability dated May 1, 2014", 6 pgs.
"International Application Serial No. PCT/US2012/059426, International Search Report dated Feb. 28, 2013", 4 pgs.
"International Application Serial No. PCT/US2012/059426, Written Opinion dated Feb. 28, 2013", 4 pgs.
"European Application Serial No. 12778185.4, Communication Pursuant to Article 94(3) EPC dated Nov. 13, 2018", 4 pgs.
U.S. Appl. No. 13/648,302, filed Oct. 10, 2012, Compressive Distal Humerus Plating System, U.S. Pat. No. 9,320,553.

\* cited by examiner

US 10,828,067 B2

COMPRESSIVE DISTAL HUMERUS PLATING SYSTEM

CROSS-REFERENCE TO RELATED APPLICATIONS

This application claims the benefit of U.S. Provisional Application No. 61/548,444, filed on Oct. 18, 2011. The entire disclosure of the above application is incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function or repair the damaged tissue. Surgical intervention can include any surgical procedure that can restore function to the damaged tissue, which can require the use of one or more orthopedic prosthesis, such as orthopedic nails, screws, implants, plates, etc., to restore function to the damaged tissue.

The present teachings relate to a plating system for use in restoring function to damaged tissue, and more specifically relates to a compressive distal humerus plating system.

SUMMARY

According to various aspects, provided is a system for compressing a fracture. The system can include a first bone plate having a first proximal end and a first distal end, and a second bone plate having a second proximal end and a second distal end. The second bone plate can be spaced apart from the first bone plate. The system can include an expansion member coupled to the second proximal end of the second bone plate. The movement of the expansion member relative to the second bone plate can cause the first distal end of the first bone plate and the second distal end of the second bone plate to move toward each other to compress the fracture.

Further provided is a system for compressing a fracture. The system can include a first bone plate having a first proximal end and a first distal end, and a second bone plate having a second proximal end and a second distal end. The system can include a first bone fastener coupled to one of the first bone plate and the second bone plate. The first bone fastener can have a bore transverse to an axis of the first bone fastener. The system can include a second bone fastener coupled to the other of the first bone plate and the second bone plate such that the second bone fastener passes through the bore of the first bone fastener.

Additionally, provided is a system for compressing a fracture. The system can include a first bone plate having a first proximal end and a first distal end. The system can also include a second bone plate having a second proximal end and a second distal end. The system can include a first bone fastener coupled to the first proximal end of the first bone plate and the second distal end of the second bone plate. The system can include a second bone fastener coupled to the first distal end of the first bone plate and the second proximal end of the second bone plate.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

DESCRIPTION OF VARIOUS ASPECTS

Figure 1:
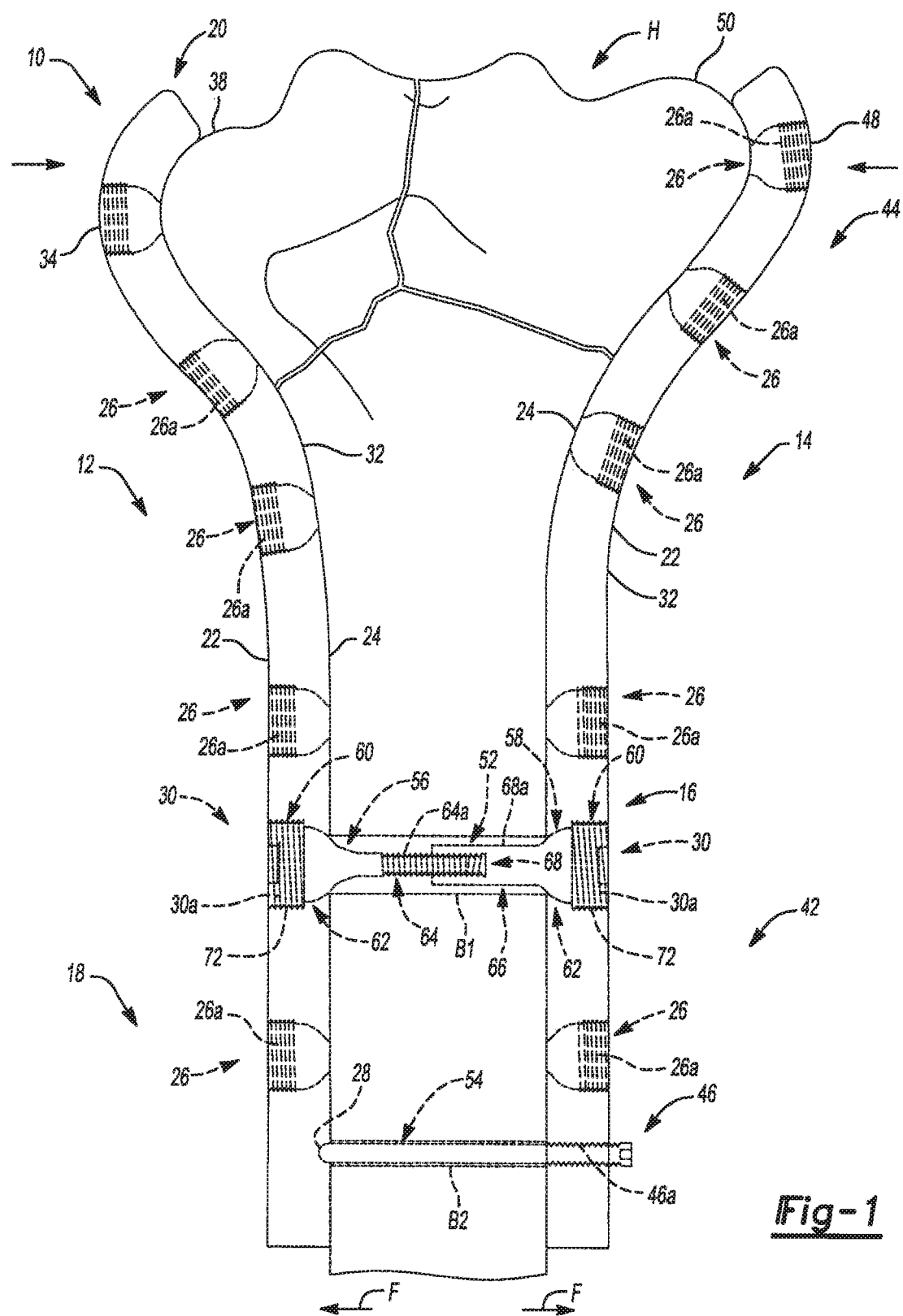
FIG. 1 is a schematic front view of an exemplary compressive distal humerus plating system according to the present teachings shown operatively associated with a distal humerus.

The following description is merely exemplary in nature and is not intended to limit the present teachings, application, or uses. It should be understood that throughout the drawings, corresponding reference numerals indicate like or corresponding parts and features. Although the following description is related generally to a plating system for use in an anatomy to restore function to damaged tissue, such as in the case of a distal humerus, it will be understood that the teachings of the system as described and claimed herein can be used in any appropriate surgical procedure. For example, the plating system described and claimed herein can be used to repair any suitable bone fracture, such as a fracture of a femur, and can be used at any location along the fractured anatomy, such as a distal end, proximal end, etc. Therefore, it will be understood that the following discussions are not intended to limit the scope of the present teachings and claims herein.

Figure 2:
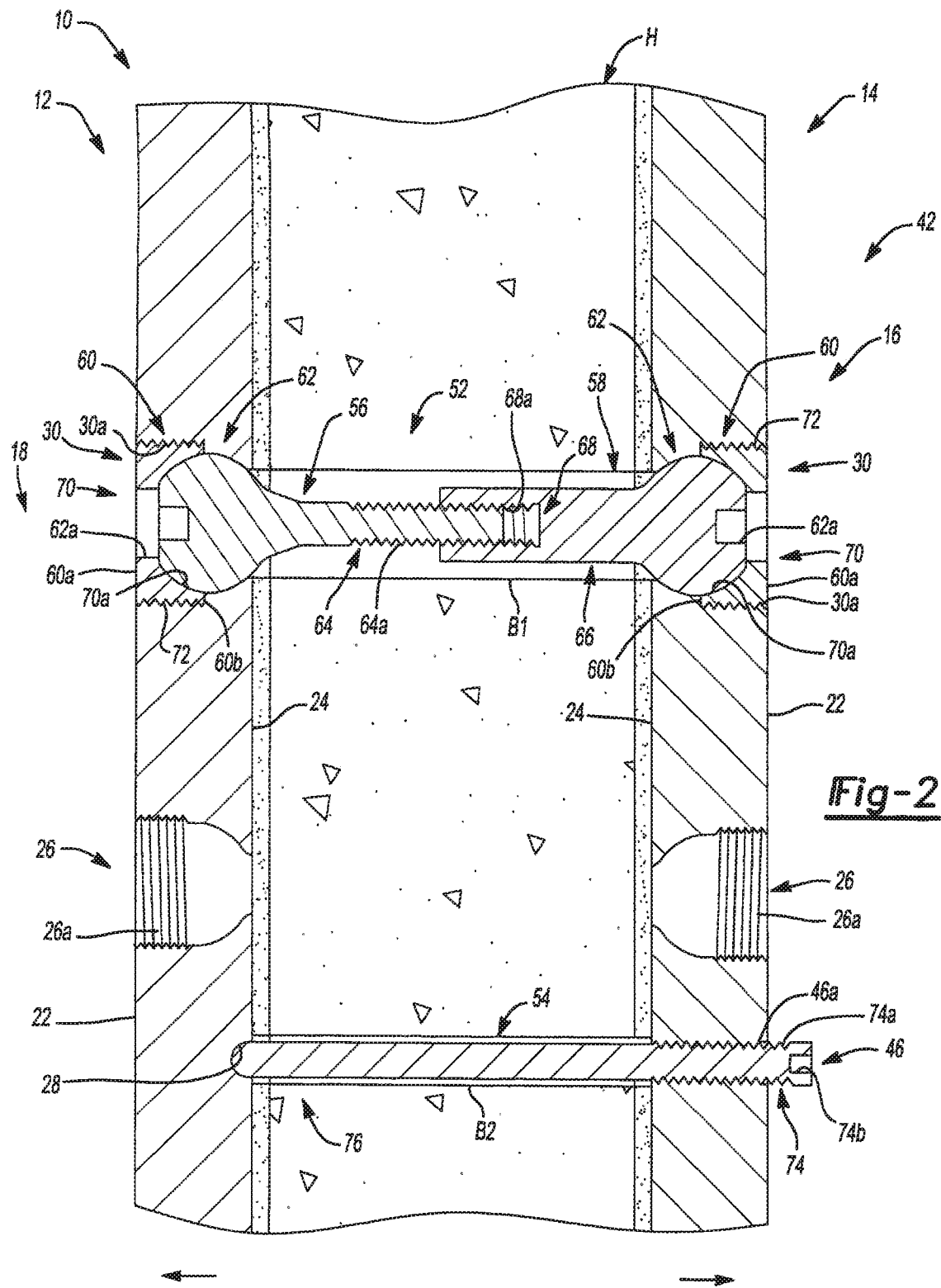
FIG. 2 is a partial cross-sectional view of the plating system of FIG. 1.

With reference to FIGS. 1 and 2, a compressive plating system 10 is shown. The compressive plating system 10 may be particularly adapted for a compressing a fracture of a distal humerus H. Various aspects of the present teachings, however, may have application for other procedures, such as to repair a pediatric femoral fracture and other fractures. One example is shown in FIGS. 1 and 2. The compressive plating system 10 can include a first plate 12, a second plate 14 and a compression system 16. In one example, the first plate 12 can be positioned substantially opposite or about 180 degrees apart from the second plate 14 about the distal humerus H. It should be noted, however, that the first plate 12 and the second plate 14 could be positioned about 90 degrees apart from each on the distal humerus H to compress a fracture of the distal humerus H using the compression system 16, if desired.

With reference to FIG. 1, the first plate 12 can have a proximal end 18, a distal end 20, a first side 22 and a second side 24. The first plate 12 can be composed of a suitable biocompatible material, such as a biocompatible metal or polymer. For example, the first plate 12 could be composed of titanium or stainless steel. The first plate 12 can include at least one or a plurality of throughbores 26, which can extend through the first side 22 and the second side 24 between the proximal end 18 and the distal end 20. The throughbores 26 can enable the receipt of one or more fasteners, such as a bone fastener, to couple the first plate 12 to the anatomy.

In one example, one or more of the throughbores 26 can include at least a portion that is generally spherical in shape, and can include a plurality of threads 26a defined about each spherically shaped throughbore 26. The plurality of threads 26a can mate with a plurality of threads formed on a head of the bone fastener to enable the bone fastener to be locked to the first plate 12. It should be noted that the head of the bone fasteners need not include a plurality of threads. In this regard, a bone fastener having an unthreaded head can seat in the throughbore 26. Further, one or more of the throughbores 26 could be devoid of the plurality of threads 26a, if desired. It should also be noted that the placement of the plurality of throughbores 26 is merely exemplary, as the throughbores 26 could be defined at any desired location along the first plate 12.

The proximal end 18 of the first plate 12 can include a recess 28 and a pivot bore 30. The recess 28 can be formed on the second side 24. In one example, the recess 28 can be formed on the second side 24 so as to not extend through the first plate 12 to the first side 22. The recess 28 can receive a portion of the compression system 16, as will be discussed in greater detail herein.

The pivot bore 30 can be defined through the proximal end 18 of the first plate 12 from the first side 22 to the second side 24. The pivot bore 30 can be substantially spherical in shape, and can include at least one or a plurality of threads 30a. The plurality of threads 30a can cooperate with a portion of the compression system 16 to couple a portion of the compression system 16 to the first plate 12.

The distal end 20 can be curved and shaped to conform to the distal humerus H. The distal end 20 can include a leading portion 32 and a curved portion 34. The leading portion 32 can transition the proximal end 18 to the curved portion 34. The curved portion 34 can be shaped to fit around a medial epicondyle 38 of the distal humerus H, for example. The shape of the distal end 20 can cooperate with the compression system 16 to enable the first plate 12 to compress the distal humerus H.

The first side 22 of the first plate 12 can be opposite the second side 24. The first side 22 can be substantially smooth. The second side 24 can be positioned adjacent to the distal humerus H when the first plate 12 is coupled to the distal humerus H. If desired, the second side 24 can be contoured to match the shape of the distal humerus H.

With continued reference to FIG. 1, as the second plate 14 can be similar to the first plate 12, only the differences between the first plate 12 and the second plate 14 will be discussed in great detail herein, and the same reference numerals will be used to denote the same or similar components. The second plate 14 can have a proximal end 42, a distal end 44, the first side 22 and the second side 24. The second plate 14 can be composed of a suitable biocompatible material, such as a biocompatible metal or polymer. For example, the second plate 14 could be composed of titanium or stainless steel. The second plate 14 can include the plurality of throughbores 26, which can enable the receipt of one or more fasteners, such as a bone fastener, to couple the second plate 14 to the anatomy.

The proximal end 42 of the second plate 14 can include a first bore 46 and the pivot bore 30. The pivot bore 30 of the second plate 14 can be substantially coaxially aligned with the pivot bore 30 of the first plate 12 to enable receipt of a portion of the compression system 16 therethrough. The first bore 46 can be coaxially aligned with the recess 28 of the first plate 12 to enable receipt of a portion of the compression system 16 therethrough. The first bore 46 can be formed through the first side 22 to the second side 24. The first bore 46 can include at least one or a plurality of threads 46a. The plurality of threads 46a can threadably engage a portion of the compression system 16, as will be discussed herein.

The distal end 20 can be curved and shaped to conform to the distal humerus H. The distal end 20 can include the leading portion 32 and a curved portion 48. The curved portion 48 can be shaped to fit around a lateral epicondyle 50 of the distal humerus H. The shape of the distal end 20 can cooperate with the compression system 16 to enable the second plate 14 to compress the distal humerus H.

With reference to FIGS. 1 and 2, the compression system 16 can cooperate with the first plate 12 and the second plate 14 to compress the fracture of the distal humerus H. The compression system 16 can include a pivot device 52 and an expansion member or compression device 54. The pivot device 52 can cooperate with the first plate 12 and the second plate 14 to enable the first plate 12 and the second plate 14 to pivot to assist in compression. The pivot device 52 can include a first pivot member 56, a second pivot member 58 and at least one screw head cap 60. The first pivot member 56 and the second pivot member 58 can be received within a first bore B1 formed through the distal humerus H.

The first pivot member 56 can include a head 62 and a shank 64. The head 62 can be substantially spherical for receipt in the pivot bore 30 of the first plate 12. The head 62 can be generally smooth. The head 62 can include a driver engagement feature 62a, which can enable a suitable tool to be used to couple the first pivot member 56 into the second pivot member 58, as will be discussed herein. The shank 64 can extend from the head 62. The shank 64 can include a plurality of threads 64a. The plurality of threads 64a can threadably engage the second pivot member 58.

As the second pivot member 58 can be similar to the first pivot member 56, only the differences between the first pivot member 56 and the second pivot member 58 will be discussed in great detail herein, and the same reference numerals will be used to denote the same or similar components. The second pivot member 58 can include the head 62 and a shank 66. The head 62 can be received in the pivot bore 30 of the second plate 14. The shank 66 can extend from the head 62. The shank 66 can include a counterbored aperture 68. The counterbored aperture 68 can include a plurality of threads 68a. The plurality of threads 68a can threadably engage the plurality of threads 64a of the first pivot member 56 to threadably couple the first pivot member 56 to the second pivot member 58.

As best shown in FIG. 2, the screw head cap 60 can be substantially circular in shape, and can include a bore 70 and a plurality of threads 72. The screw head cap 60 can be received over the head 62 of the first pivot member 56 and the second pivot member 58 to retain the first pivot member 56 and the second pivot member 58 within the pivot bore 30. The bore 70 can be defined from a first surface 60a to a second surface 60b. The bore 70 can have a spherical taper 70a, which can be shaped to mate with the spherical head 62. The plurality of threads 72 can extend along a circumference of the screw head cap 60 from the first surface 60a to the second surface 60b. The plurality of threads 72 can engage the plurality of threads 30a of the pivot bore 30 to retain the first pivot member 56 and the second pivot member 58 within the pivot bore 30.

The compression device 54 can be received through a second bore B2 formed in the distal humerus H. The compression device 54 can be composed of a suitable biocompatible material, such as a biocompatible metal. In one example, the compression device 54 can comprise a pin. The compression device 54 can include a first end 74 and a second end 76. The first end 74 can include a plurality of threads 74a and a driver engagement feature 74b. The plurality of threads 74a can threadably engage the plurality of threads 46a of the first bore 46 to enable the compression device 54 to be threadably advanced through the second bore B2. The second end 76 can be rounded and smooth for receipt in the recess 28. The compression device 54 can be received through the first bore 46 such that the plurality of threads 74a can engage the plurality of threads 46a of the first bore 46 to advance the compression device 54 within the first bore 46. Advancement of the compression device 54 can push against the proximal end 18 of the first plate 12. With reference to FIG. 1, this application of force between the first plate 12 and the second plate 14 can cause the distal end 20 of the first plate 12 to move toward the distal humerus H, thereby compressing the fracture of the distal humerus H.

In order to couple the compressive plating system 10 to an anatomy, such as the distal humerus H, an incision can be made adjacent to the distal humerus H. In one exemplary method, with reference to FIG. 1, the first plate 12 can be positioned adjacent to the distal humerus, such that the curved portion 34 is adjacent to the medial epicondyle 38. One or more bone fasteners can be inserted through the one or more throughbores 26 of the first plate 12 to couple the first plate 12 to the anatomy. The second plate 14 can be positioned opposite the first plate 12 such that the curved portion 48 is adjacent to the lateral epicondyle 50. One or more bone fasteners can be inserted through the one or more throughbores 26 of the second plate 14 to couple the second plate 14 to the anatomy. With or without the use of a guide wire, a first bore B1 can be formed through the distal humerus H, using the pivot bores 30 of the first plate 12 and the second plate 14 as guides.

Then, the first pivot member 56 and the second pivot member 58 can be inserted into the first bore B1 so that the head 62 of the first pivot member 56 and the head 62 of the second pivot member 58 rest within the pivot bores 30. The first pivot member 56 can be threaded into engagement with the second pivot member 58 via a tool engaged with at least one of the driver engagement features 62a of the head 62 of the first pivot member 56 and the head 62 of the second pivot member 58. Then, screw head caps 60 can be threadably coupled to the pivot bores 30 to rotatably retain the first pivot member 56 and the second pivot member 58 within the first bore B1.

With or without the use of a guide wire, with reference to FIG. 2, the second bore B1 can be drilled through the distal humerus H from the first bore 46 to the recess 28. Then, the compression device 54 can be inserted through the first bore 46, and the plurality of threads 72 of the compression device 54 can threadably engage the plurality of threads 46a of the first bore 46. Threaded advancement of the compression device 54 within the first bore 46 can cause the second end 76 of the compression device 54 to contact the recess 28. The continued advancement of the compression device 54 can cause the proximal end 18 of the first plate 12 and the second plate 14 to move outwardly, as illustrated in FIG. 1. The pivot device 52 constrains the movement of the first plate 12 and the second plate 14, thus, the force against the proximal end 18 of the first plate 12 and the proximal end 42 of the second plate 14 causes the distal end 20 of the first plate 12 to move toward the distal end 44 of the second plate 14 to compress a fracture in the distal humerus H.

Figure 3:
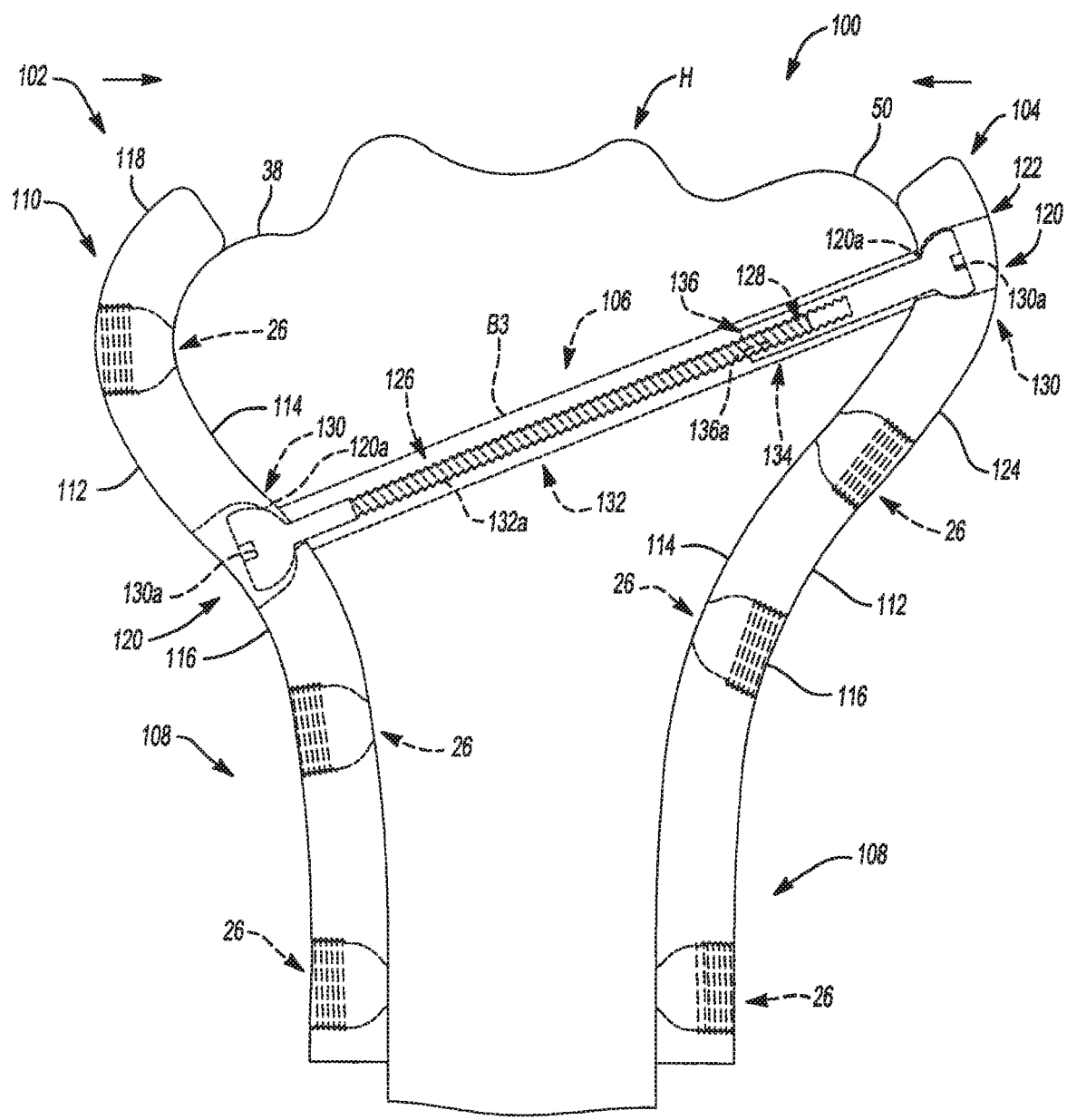
FIG. 3 is a schematic front view of another exemplary compressive distal humerus plating system for use with a distal humerus according to the present teachings.
Figure 4:
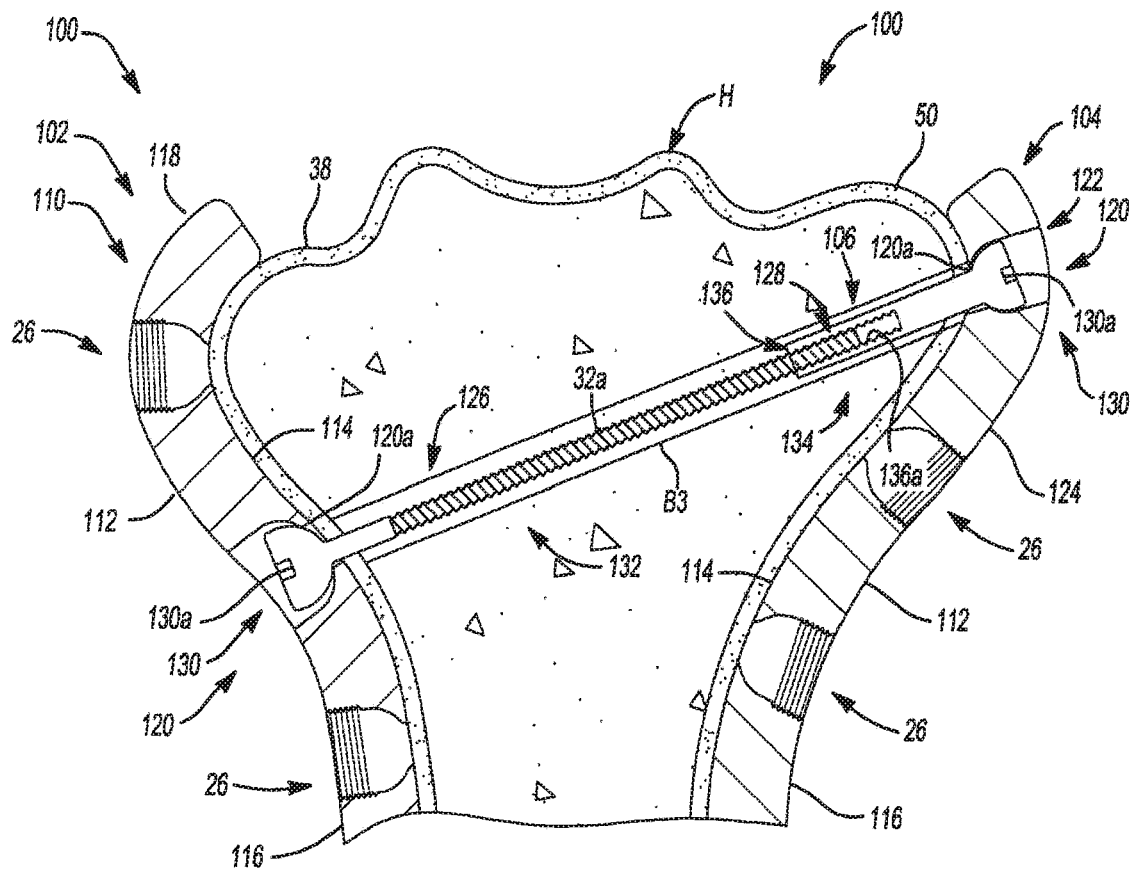
FIG. 4 is a partial cross-sectional view of the plating system of FIG. 3.

With reference now to FIGS. 3 and 4, in one example, a compressive plating system 100 can be employed to repair a damaged portion of an anatomy. As the compressive plating system 100 can be similar to the compressive plating system 10 described with reference to FIGS. 1 and 2, only the differences between the compressive plating system 10 and the compressive plating system 100 will be discussed in great detail herein, and the same reference numerals will be used to denote the same or similar components. With reference to FIGS. 3 and 4, the compressive plating system 100 can include a first plate 102, a second plate 104 and a compression system 106. In one example, the first plate 102 can be positioned opposite or about 180 degrees apart from the second plate 104 about the distal humerus H.

With reference to FIG. 3, the first plate 102 can have a proximal end 108, a distal end 110, a first side 112 and a second side 114. The first plate 102 can be composed of a suitable biocompatible material, such as a biocompatible metal or polymer. For example, the first plate 102 could be composed of titanium or stainless steel. The first plate 102 can include the plurality of throughbores 26, which can extend through the first side 112 and the second side 114 between the proximal end 108 and the distal end 110. As discussed, the throughbores 26 can each receive a bone fastener to couple the first plate 102 to the distal humerus H.

The distal end 110 can be curved and shaped to conform to the distal humerus H. The distal end 110 can include a leading portion 116 and a curved portion 118. The leading portion 116 can transition the proximal end 108 to the curved portion 118. The curved portion 118 can be shaped to fit around the medial epicondyle 38 of the distal humerus H. The curved portion 118 can include a bore 120. The bore 120 can be substantially spherical, and can taper to an aperture 120a. The aperture 120a can enable the receipt of a portion of the compression system 106 to be positioned therethrough. In one example, the bore 120 can taper to an elongated slot, which can enable a portion of the compression system 106 to be positioned at any desired angle relative to the first plate 102. Alternatively, the bore 120 can taper to a circular aperture.

The first side 112 of the first plate 102 can be opposite the second side 114. The first side 112 can be substantially smooth. The second side 114 can be positioned adjacent to the distal humerus H when the first plate 102 is coupled to the distal humerus H. If desired, the second side 114 can be contoured to match the shape of the distal humerus H.

As the second plate 104 can be similar to the first plate 102, only the differences between the first plate 102 and the second plate 104 will be discussed in great detail herein, and the same reference numerals will be used to denote the same or similar components. The second plate 104 can have the proximal end 108, a distal end 122, the first side 112 and the second side 114. The second plate 104 can be composed of a suitable biocompatible material, such as a biocompatible metal or polymer. For example, the second plate 104 could be composed of titanium or stainless steel. The second plate 104 can include the plurality of throughbores 26, which can extend through the first side 112 and the second side 114 between the proximal end 108 and the distal end 122. As discussed, the throughbores 26 can each receive a bone fastener to couple the second plate 104 to the distal humerus H.

The distal end 122 can be curved and shaped to conform to the distal humerus H. The distal end 122 can include the leading portion 116 and a curved portion 124. The curved portion 124 can be shaped to fit around the lateral epicondyle 50 of the distal humerus H. The curved portion 124 can include the bore 120.

The compression system 106 can cooperate with the first plate 102 and the second plate 104 to compress a distal humerus fracture. The compression system 106 can include a first member 126 and a second member 128. The first member 126 can have a head 130 and a shank 132. The head 130 can be substantially spherical to mate with the bore 120. It should be noted, however, that although the compression system 106 is described and illustrated herein as being received through the bores 120, the compression system 106 could also be received through any opposed throughbores 26. The head 130 can include a driver engagement feature 130a, for receipt of a suitable instrument to drive the first member 126 into engagement with the second member 128, as will be discussed herein. The head 130 can be generally smooth. It should be noted that the head 130 could include a plurality of threads for mating with a plurality of threads formed in the bore 120, if desired. The shank 132 can extend from the head 130. The shank 132 can include a plurality of threads 132a. The plurality of threads 132a can threadably engage the second member 128.

As the second member 128 can be similar to the first member 126, only the differences between the first member 126 and the second member 128 will be discussed in great detail herein, and the same reference numerals will be used to denote the same or similar components. The second member 128 can include the head 130 and a shank 134. The head 130 can be received in the bore 120 of the second plate 104. The shank 134 can extend from the head 130. The shank 134 can include a counterbored aperture 136. The counterbored aperture 136 can include a plurality of threads 136a. The plurality of threads 136a can threadably engage the plurality of threads 132a of the first member 126 to threadably couple the first member 126 to the second member 128.

In order to couple the compressive plating system 100 to an anatomy, such as the distal humerus H, an incision can be made adjacent to the distal humerus H. In one exemplary method, with reference to FIG. 3, the first plate 102 can be positioned adjacent to the distal humerus H, such that the curved portion 118 is adjacent to the medial epicondyle 38. One or more bone fasteners can be inserted through the one or more throughbores 26 of the first plate 102 to couple the first plate 102 to the anatomy. The second plate 104 can be positioned opposite the first plate 102 such that the curved portion 124 is adjacent to the lateral epicondyle 50. One or more bone fasteners can be inserted through the one or more throughbores 26 of the second plate 104 to couple the second plate 104 to the anatomy.

In one example, a guide wire can be positioned between the bore 120 of the first plate 102 and the bore 120 of the second plate 104. If either or both of the bores 120 taper to a slot, then the guide wire can be orientated at any desired angle to form a bore B3 through the distal humerus H. Then, a drill bit can be passed over the guide wire to form the bore B3 in the anatomy. The first member 126 and the second member 128 can be inserted into a respective one of the bore 120 of the first plate 102 and the bore 120 of the second plate 104. Then, a suitable tool can be engaged with the driver engagement features 130a to threadably engage the first member 126 with the second member 128. The continued advancement of the first member 126 within the second member 128 can compress a fracture at the distal humerus H.

Figure 5:
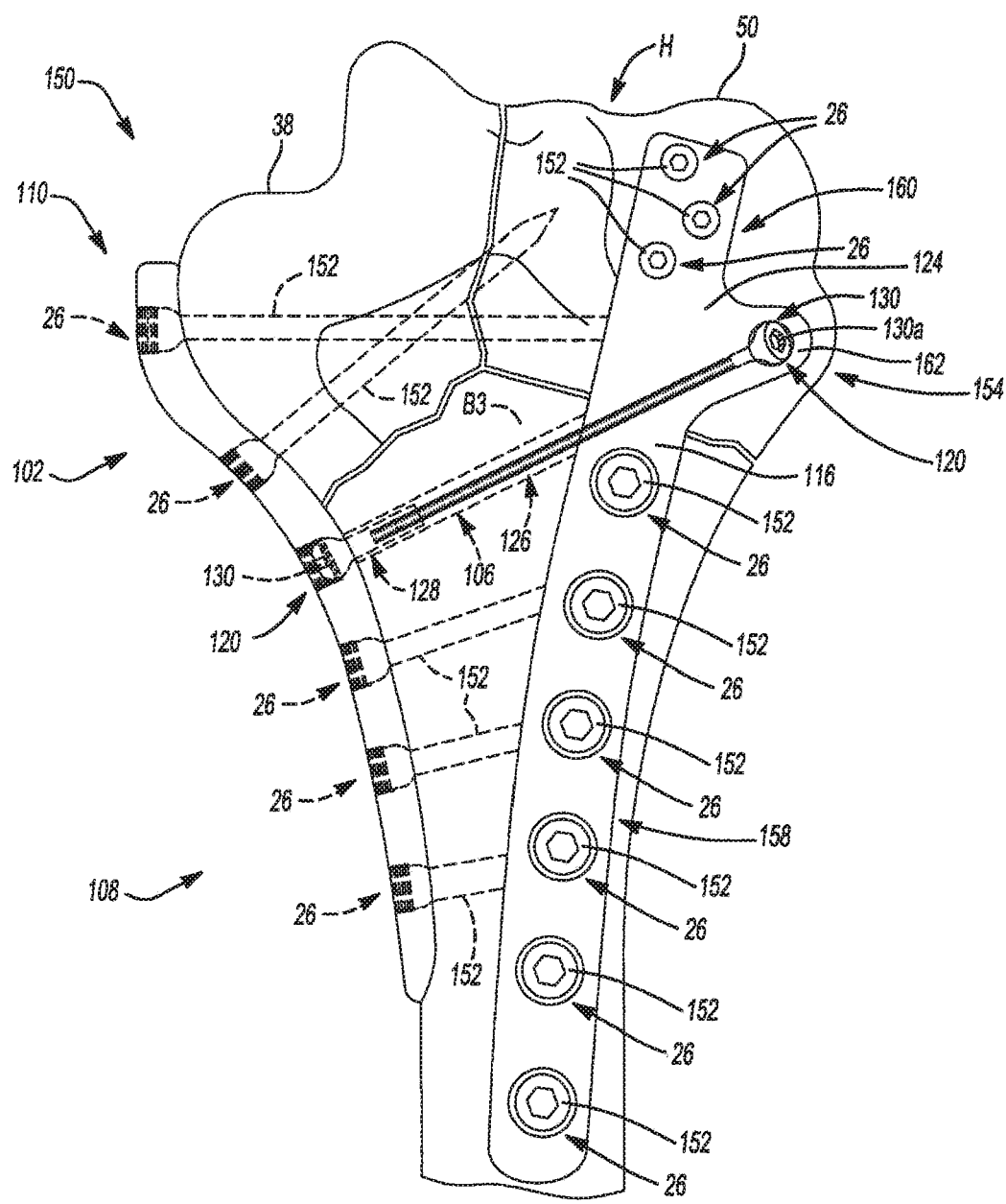
FIG. 5 is a schematic perspective illustration of another exemplary compressive distal humerus plating system for use with a distal humerus according to the present teachings.

Alternatively, with reference to FIG. 5, in one example, a compressive plating system 150 can be employed to repair a damaged portion of an anatomy. As the compressive plating system 150 can be similar to the compressive plating system 100 described with reference to FIGS. 3 and 4, only the differences between the compressive plating system 100 and the compressive plating system 150 will be discussed in great detail herein, and the same reference numerals will be used to denote the same or similar components. With reference to FIG. 5, the compressive plating system 150 can include the first plate 102, a second plate 154 and the compression system 106. In one example, the first plate 102 can be positioned about 90 degrees apart from the second plate 154 about the distal humerus H, and the compression system 106 can be used to compress a fracture of the distal humerus H. A plurality of bone fasteners 152 can also be inserted through the throughbores 26 of the first plate 102 and the second plate 154 to couple the first plate 102 and the second plate 154 to the anatomy.

The second plate 154 can have a proximal end 158, the distal end 160, the first side 112 and the second side 114. The proximal end 158 of the second plate 154 can have a longer length than the proximal end 108 of the first plate 102. It should be noted that the proximal end 158 of the second plate 154 could have the same length as the proximal end 108 of the first plate 102, or the proximal end 108 of the first plate 102 could have a length longer than the proximal end 158 of the second plate 154.

The distal end 160 can be curved and shaped to conform to the distal humerus H. The distal end 160 can include the leading portion 116, the curved portion 124 and a flange 162. The flange 162 can extend outwardly from the curved portion 124 of the distal end 160 of the second plate 154. The flange 162 can be curved, and can include the bore 120. It should be noted that the flange 162 can have any desired shape and can extend outwardly at any desired location along the length of the second plate 154. In addition, the second plate 154 need not include the flange 162, as the bore 120 can be formed through the distal end 160 of the second plate 154.

In this example, the first member 126 can be inserted through the bore 120 of the flange 162 of the second plate 154, and the second member 128 can be inserted through the bore 120 of the first plate 102. Thus, the compression system 106 can be used to compress a fracture of the distal humerus H when the first plate 102 and the second plate 154 are about 90 degrees offset from each other about the distal humerus H.

Figure 6:
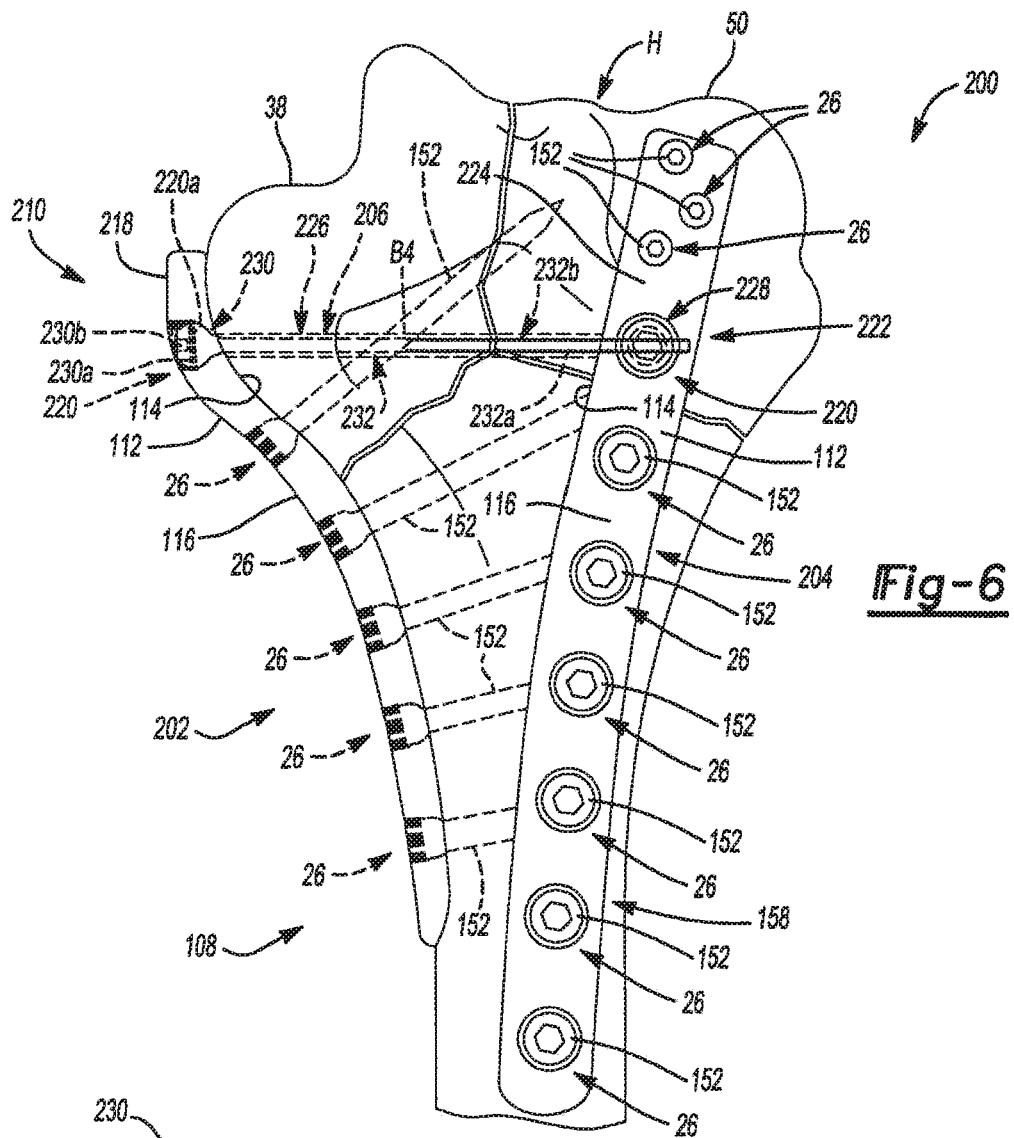
FIG. 6 is a schematic perspective illustration of another exemplary compressive distal humerus plating system for use with a distal humerus according to the present teachings.
Figure 7:
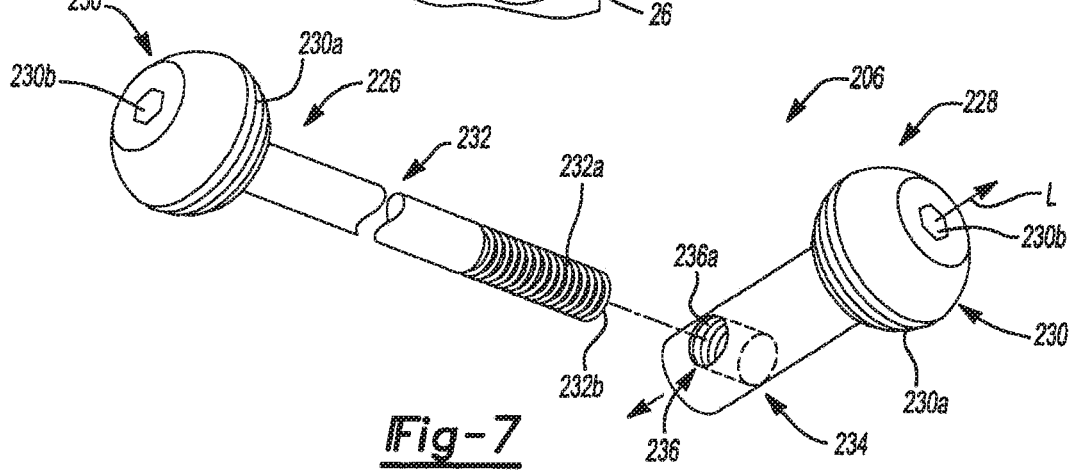
FIG. 7 is a perspective view of a compression system for use with the compressive distal humerus plating system of FIG. 6.

With reference now to FIGS. 6 and 7, in one example, a compressive plating system 200 can be employed to repair a damaged portion of an anatomy. As the compressive plating system 200 can be similar to the compressive plating system 150 described with reference to FIG. 5, only the differences between the compressive plating system 150 and the compressive plating system 200 will be discussed in great detail herein, and the same reference numerals will be used to denote the same or similar components. With reference to FIG. 6, the compressive plating system 200 can include a first plate 202, a second plate 204 and a compression system 206. In one example, the first plate 202 can be positioned about 90 degrees apart from the second plate 204 about the distal humerus H.

The first plate 202 can have the proximal end 108, a distal end 210, the first side 112 and the second side 114. The first plate 202 can be composed of a suitable biocompatible material, such as a biocompatible metal or polymer. For example, the first plate 202 could be composed of titanium or stainless steel. The first plate 202 can include the plurality of throughbores 26, which can extend through the first side 112 and the second side 114 between the proximal end 108 and the distal end 210. The plurality of bone fasteners 152 can also be inserted through the throughbores 26 of the first plate 102 to couple the first plate 102 to the anatomy.

The distal end 210 can be curved and shaped to conform to the distal humerus H. The distal end 210 can include the leading portion 116 and a curved portion 218. The curved portion 218 can be shaped to fit around the medial epicondyle 38 of the distal humerus H. The curved portion 218 can include a bore 220. The bore 220 can be substantially spherical, and can include a plurality of threads 220a. The bore 220 can enable a portion of the compression system 206 to be positioned therethrough.

As the second plate 204 can be similar to the first plate 202, only the differences between the first plate 202 and the second plate 204 will be discussed in great detail herein, and the same reference numerals will be used to denote the same or similar components. With reference to FIG. 6, the second plate 204 can have the proximal end 158, a distal end 222, the first side 112 and the second side 114. The second plate 204 can be composed of a suitable biocompatible material, such as a biocompatible metal or polymer. For example, the second plate 204 could be composed of titanium or stainless steel. The second plate 204 can include the plurality of throughbores 26, which can extend through the first side 112 and the second side 114 between the proximal end 158 and the distal end 222. The plurality of bone fasteners 152 can also be inserted through the throughbores 26 of the second plate 204 to couple the second plate 204 to the anatomy.

The distal end 222 can be curved and shaped to conform to the distal humerus H. The distal end 222 can include the leading portion 116 and a curved portion 224. The curved portion 224 can be shaped to correspond with the lateral epicondyle 50 of the distal humerus H. The curved portion 224 can include the bore 220.

With reference to FIGS. 6 and 7, the compression system 206 can cooperate with the first plate 202 and the second plate 204 to compress a distal humerus fracture. The compression system 206 can include a first bone fastener or member 226 and a second bone fastener or member 228. The first member 226 can have a head 230 and a shank 232. The head 230 can be substantially spherical to mate with the bore 220. It should be noted, however, that although the compression system 206 is described and illustrated herein as being received through the bores 220, the compression system 206 could also be received through any opposed throughbores 26.

The head 230 can include a plurality of threads 230a and a driver engagement feature 230b. The plurality of threads 230a can threadably engage the plurality of threads 220a of the bore 220 to fixedly couple the first member 226 to the bore 220. The driver engagement feature 230b can receive a suitable instrument to drive the first member 226 into engagement with the second member 228, as will be discussed herein. The shank 232 can extend from the head 230. The shank 232 can include a plurality of threads 232a at a distal end 232b. The plurality of threads 232a can threadably engage the second member 228.

With reference to FIG. 7, as the second member 228 can be similar to the first member 226, only the differences between the first member 226 and the second member 228 will be discussed in great detail herein, and the same reference numerals will be used to denote the same or similar components. The second member 228 can include the head 230 and a shank 234. The head 230 can be received in the bore 220 of the second plate 204. The shank 234 can extend from the head 230. The shank 234 can include a cross bore 236. The cross bore 236 can be formed substantially perpendicular to a longitudinal axis L of the second member 228. The cross bore 236 can include a plurality of threads 236a. The plurality of threads 236a can threadably engage the plurality of threads 232a of the first member 226 to threadably couple the first member 226 to the second member 228.

In order to couple the compressive plating system 200 to an anatomy, such as the distal humerus H, an incision can be made adjacent to the distal humerus H. In one exemplary method, with reference to FIG. 6, the first plate 202 can be positioned adjacent to the distal humerus H, such that the curved portion 218 is adjacent to the medial epicondyle 38. One or more bone fasteners 152 can be inserted through the one or more throughbores 26 of the first plate 202 to couple the first plate 202 to the anatomy. The second plate 204 can be positioned about 90 degrees from the first plate 102 such that the curved portion 224 is adjacent to the lateral epicondyle 50. One or more bone fasteners 152 can be inserted through the one or more throughbores 26 of the second plate 204 to couple the second plate 204 to the anatomy.

In one example, the second member 228 can be inserted into the second plate 204 such that the plurality of threads 230a of the head 230 threadably engage the plurality of threads 220a of the bore 220. Then, a guide wire can be positioned between the bore 220 of the first plate 202 and the cross bore 236 of the second member 228. Then, a drill bit can be passed over the guide wire to form a bore B4 in the anatomy. The first member 226 can be inserted into the bore 220 of the first plate 202 so that the plurality of threads 230a of the head 230 threadably engage the plurality of threads 220a of the bore 220 and the plurality of threads 232a of the shank 232 threadably engage the plurality of threads 236a of the cross bore 236. The engagement between the first member 226 and the second member 228 can compress the fracture of the distal humerus H.

Figure 8:
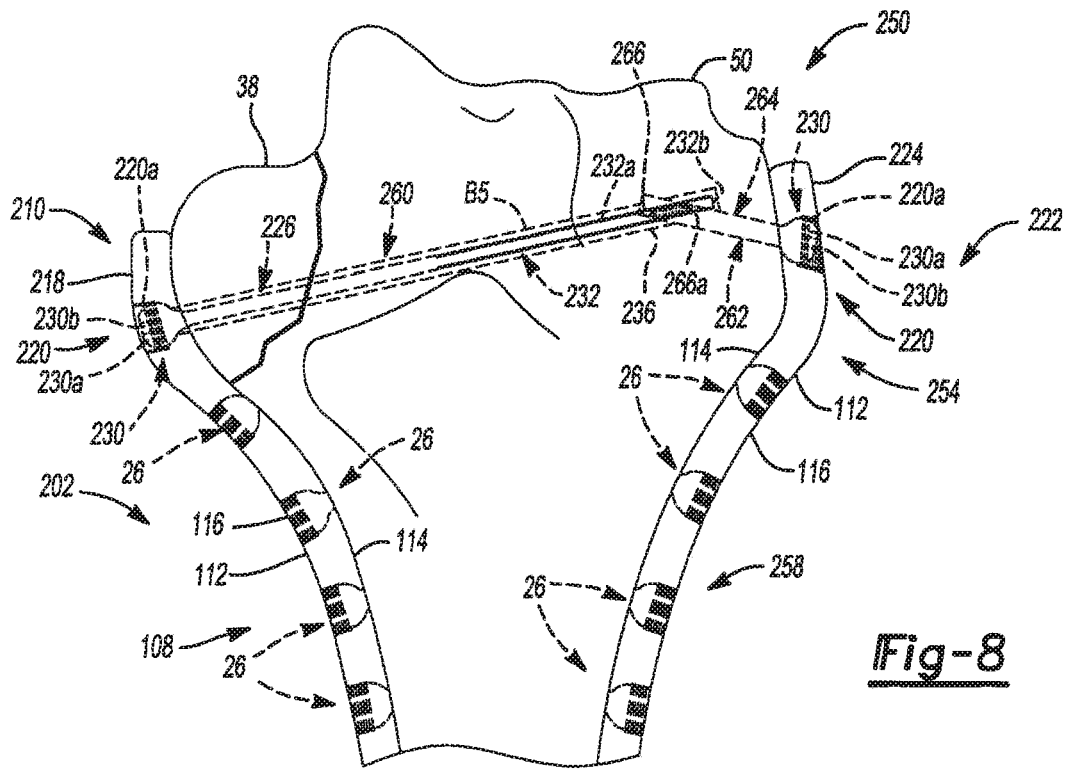
FIG. 8 is a schematic front view of another exemplary compressive distal humerus plating system for use with a distal humerus according to the present teachings.

With reference now to FIG. 8, in one example, a compressive plating system 250 can be employed to repair a damaged portion of an anatomy. As the compressive plating system 250 can be similar to the compressive plating system 200 described with reference to FIGS. 6 and 7, only the differences between the compressive plating system 200 and the compressive plating system 250 will be discussed in great detail herein, and the same reference numerals will be used to denote the same or similar components. With reference to FIG. 8, the compressive plating system 200 can include the first plate 202, a second plate 254 and the compression system 260. In one example, the first plate 202 can be positioned about 180 degrees apart from the second plate 254 about the distal humerus H.

The second plate 254 can have a proximal end 258, the distal end 222, the first side 112 and the second side 114. The proximal end 258 can have about the same length as the proximal end 108 of the first plate 202. It should be noted that the proximal end 258 of the second plate 254 could have a different length than the proximal end 108 of the first plate 202, if desired.

With continued reference to FIG. 8, the compression system 260 can cooperate with the first plate 202 and the second plate 254 to compress a distal humerus fracture. The compression system 260 can include the first bone fastener or member 226 and a second bone fastener or member 262. It should be noted, that although the compression system 260 is described and illustrated herein as being received through the bores 220, the compression system 260 could also be received through any opposed throughbores 26.

The second member 262 can be similar to the first member 226, only the differences between the first member 226 and the second member 262 will be discussed in great detail herein, and the same reference numerals will be used to denote the same or similar components. The second member 262 can include the head 230 and a shank 264. The shank 164 can extend from the head 230. The shank 264 can include a cross slot 266. The cross slot 266 is illustrated as being formed at an angle relative to the longitudinal axis L of the second member 228, but could formed substantially perpendicular to a longitudinal axis L of the second member 228, if desired. Further, it should be noted that although the cross slot 266 is illustrated as comprising a slot, the cross slot 266 could comprise a bore, if desired. The cross slot 266 can include a plurality of threads 266a. The plurality of threads 266a can threadably engage the plurality of threads 232a of the first member 226 to threadably couple the first member 226 to the second member 262.

In this example, in order to compress a fracture, the second member 262 can be inserted through the bore 220 of the second plate 254 such that the plurality of threads 230a of the head 230 threadably engage the plurality of threads 220a of the bore 220. Then, a guide wire can be positioned between the bore 220 of the first plate 202 and the cross slot 266 of the second member 262. Then, a drill bit can be passed over the guide wire to form a bore B5 in the anatomy. The first member 226 can be inserted into the bore 220 of the first plate 202 so that the plurality of threads 230a of the head 230 threadably engage the plurality of threads 220a of the bore 220 and the plurality of threads 232a of the shank 232 threadably engage the plurality of threads 266a of the cross slot 266. The engagement between the first member 226 and the second member 262 can compress the fracture of the distal humerus H. Thus, the compression system 260 can be used to compress a fracture of the distal humerus H when the first plate 202 and the second plate 254 are about 180 degrees offset from each other about the distal humerus H.

Figure 9:
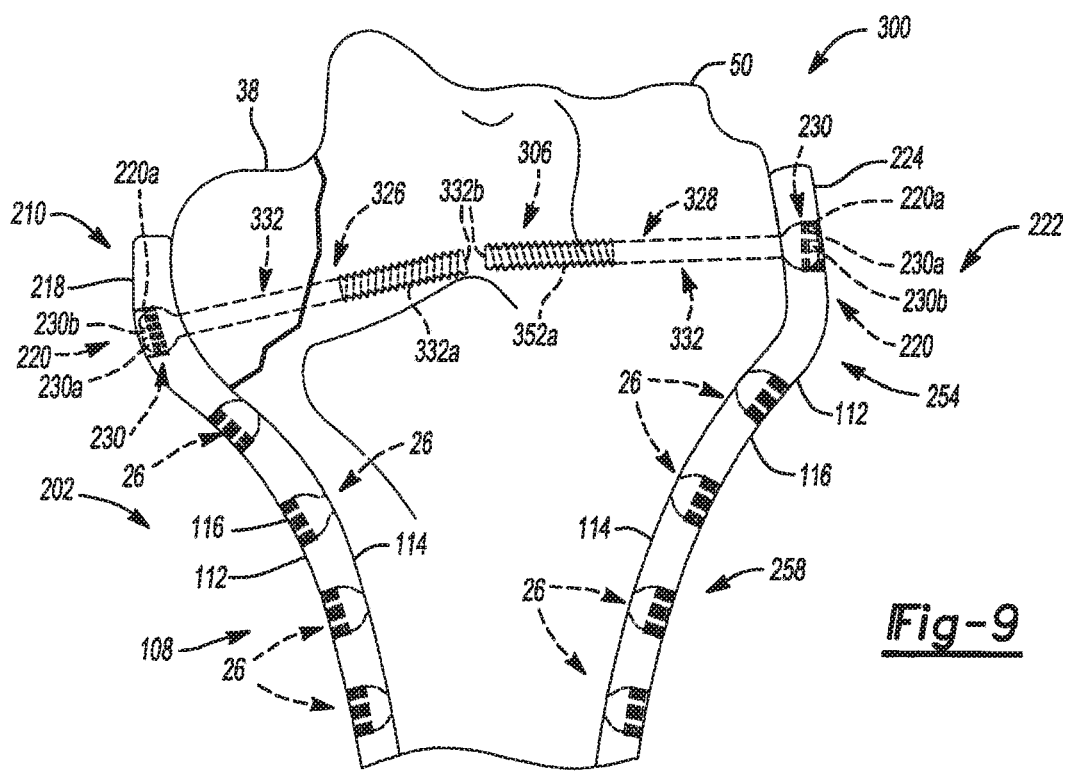
FIG. 9 is a schematic front view of another exemplary compressive distal humerus plating system for use with a distal humerus according to the present teachings.

With reference now to FIG. 9, in one example, a compressive plating system 300 can be employed to repair a damaged portion of an anatomy. As the compressive plating system 300 can be similar to the compressive plating system 250 described with reference to FIG. 8, only the differences between the compressive plating system 250 and the compressive plating system 300 will be discussed in great detail herein, and the same reference numerals will be used to denote the same or similar components. With continued reference to FIG. 9, the compressive plating system 300 can include the first plate 202, the second plate 254 and a compression system 306. In one example, the first plate 202 can be positioned about 180 degrees apart from the second plate 254 about the distal humerus H. It should be noted that although not illustrated herein, the first plate 202 could be orientated about 90 degrees apart from the second plate 254 about the distal humerus H, and the compression system 306 could be used to compress a fracture of the distal humerus H.

The compression system 306 can cooperate with the first plate 202 and the second plate 254 to compress a distal humerus fracture. The compression system 306 can include a first member 326 and a second member 328. The first member 326 and the second member 328 can be magnetic, and in one example, can be composed of a biocompatible rare earth magnetic material so as to comprise permanent magnets. In one example, the first member 326 can comprise a north pole, while the second member 328 can comprise a south pole. The north pole of the first member 326 can be attracted to the south pole of the second member 328 to compress the distal humerus H.

The first member 326 and the second member 328 can each have the head 230 and a shank 332. The head 230 can be substantially spherical to mate with the bore 220. It should be noted, however, that although the compression system 306 is described and illustrated herein as being received through the bores 220, the compression system 306 could also be received through any opposed throughbores 26. The shank 332 can extend from the head 230. The shank 332 can include a plurality of threads 332a at a distal end 332b. The plurality of threads 332a can enable the advancement of the first member 326 and the second member 328 through the anatomy.

In order to couple the compressive plating system 300 to an anatomy, such as the distal humerus H, an incision can be made adjacent to the distal humerus H. In one exemplary method, the first plate 202 can be positioned adjacent to the distal humerus H, such that the curved portion 218 is adjacent to the medial epicondyle 38. As discussed previously, one or more bone fasteners can be inserted through the one or more throughbores 26 of the first plate 202 to couple the first plate 202 to the anatomy. The second plate 254 can be positioned about 180 degrees from the first plate 202 such that the curved portion 224 is adjacent to the lateral epicondyle 50. One or more bone fasteners can be inserted through the one or more throughbores 26 of the second plate 254 to couple the second plate 254 to the anatomy.

In one example, the first member 326 can be inserted into the second plate 204 such that the plurality of threads 230a of the head 230 threadably engage the plurality of threads 220a of the bore 220. Then, the second member 228 can be inserted into the second plate 204 such that the plurality of threads 230a of the head 230 threadably engage the plurality of threads 220a of the bore 220. The attraction between the north pole of the first member 326 and the south pole of the second member 328 can compress the fracture of the distal humerus H.

Figure 10:
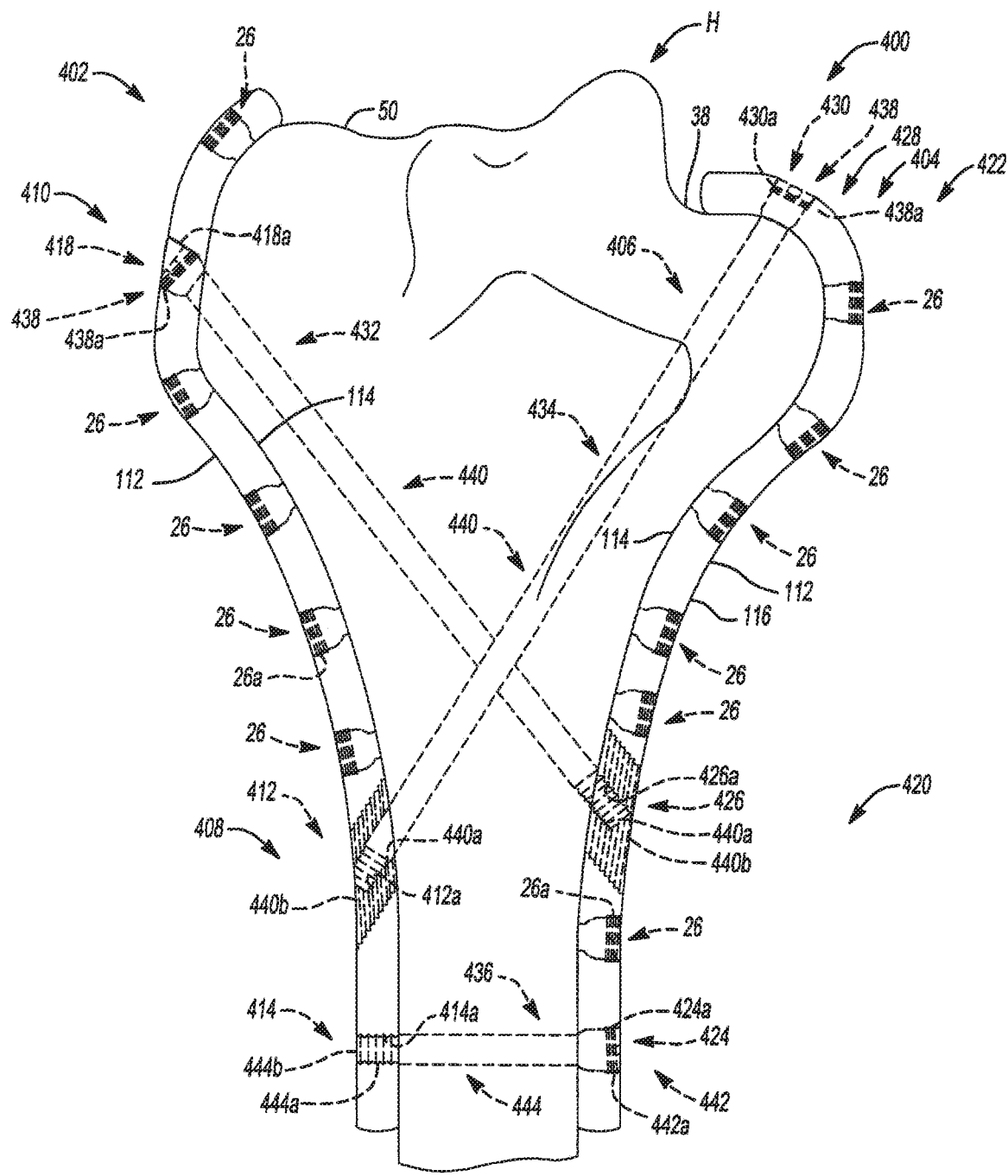
FIG. 10 is a schematic front view of an exemplary compressive distal humerus plating system for use with a distal humerus according to the present teachings.
Figure 11:
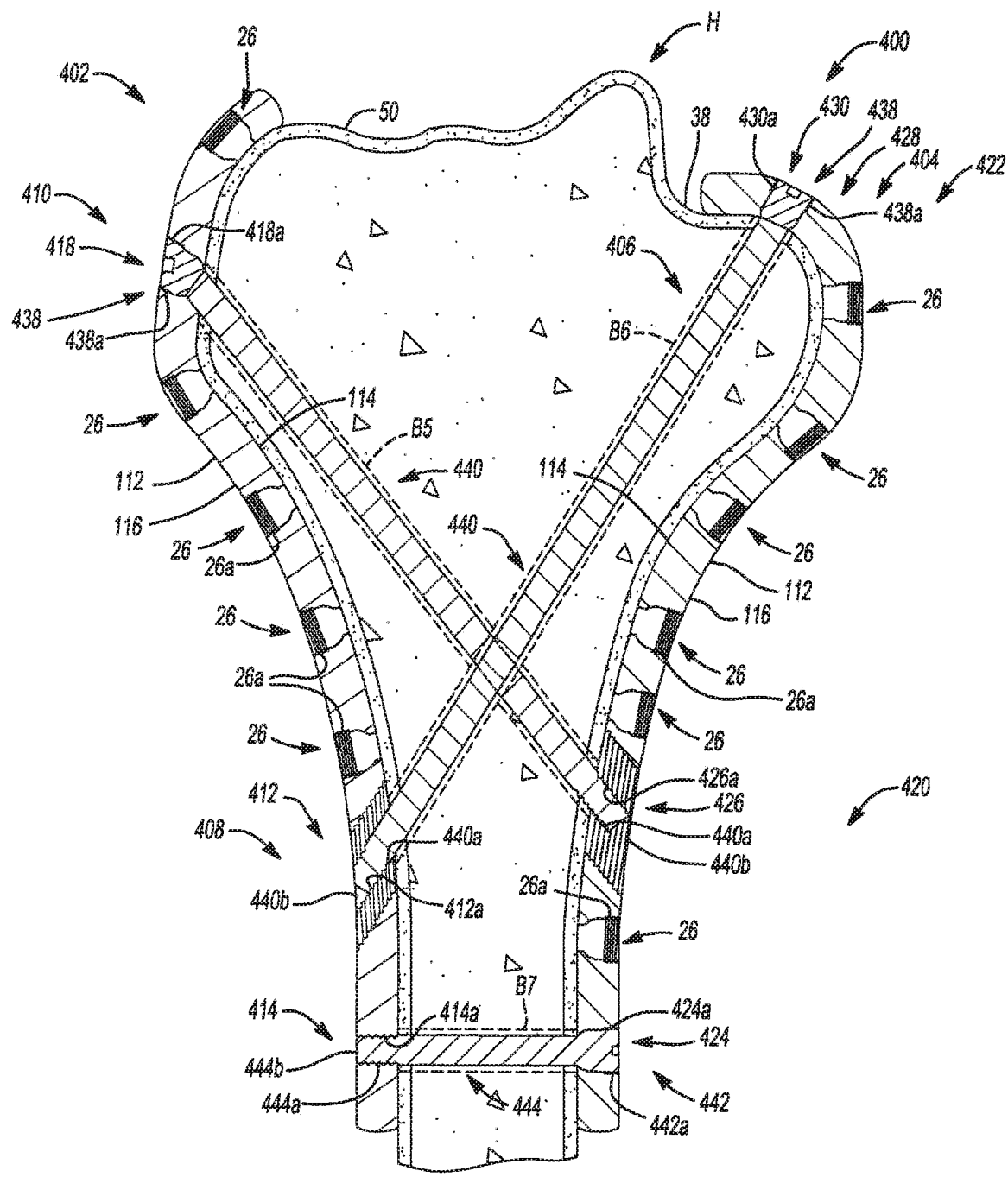
FIG. 11 is a partial cross-sectional view of the plating system of FIG. 10.

With reference now to FIGS. 10 and 11, in one example, a compressive plating system 400 can be employed to repair a damaged portion of an anatomy. As the compressive plating system 400 can be similar to the compressive plating system 100 described with reference to FIGS. 3 and 4, only the differences between the compressive plating system 100 and the compressive plating system 400 will be discussed in great detail herein, and the same reference numerals will be used to denote the same or similar components. With reference to FIGS. 10 and 11, the compressive plating system 400 can include a first plate 402, a second plate 404 and a compression system 406. In one example, the first plate 402 can be positioned opposite or about 180 degrees apart from the second plate 404 about the distal humerus H.

With reference to FIG. 10, the first plate 402 can have a proximal end 408, a distal end 410, the first side 112 and the second side 114. The first plate 402 can be composed of a suitable biocompatible material, such as a biocompatible metal or polymer. For example, the first plate 402 could be composed of titanium or stainless steel. The first plate 402 can include the plurality of throughbores 26, which can extend through the first side 112 and the second side 114 between the proximal end 408 and the distal end 410. The throughbores 26 can enable the receipt of one or more fasteners, such as a bone fastener, to couple the first plate 402 to the anatomy.

The proximal end 408 of the first plate 402 can include a first bore 412 and a second bore 414. Each of the first bore 412 and the second bore 414 can be defined through the first plate 402 from the first side 112 to the second side 114. One or more of the first bore 412 and the second bore 414 can comprise slots, which can enable the compression system 406 to be coupled to the anatomy at various orientations. Each of the first bore 412 and the second bore 414 can comprise a plurality of teeth or partial threads 412a, 414a, which can assist in fixedly coupling or locking a portion of the compression system 406 to the first plate 402. Alternatively, the first bore 412 and the second bore 414 can comprise a smooth circular bore.

The distal end 410 can be curved and shaped to conform to the distal humerus H. The distal end 410 can include the leading portion 116 and a curved portion 416. The curved portion 416 can be shaped to fit around the lateral epicondyle 50 of the distal humerus H. The shape of the distal end 410 can cooperate with the compression system 406 to enable the first plate 402 to compress the distal humerus H. The curved portion 416 can include a first compression bore 418. The first compression bore 418 can receive a portion of the compression system 406 to assist in compressing a fracture of the distal humerus H. The first compression bore 418 can include a plurality of threads 418a, which can threadably engage a portion of the compression device 406 to fixedly couple or lock the portion of the compression device 406 to the first plate 402.

With continued reference to FIGS. 10 and 11, as the second plate 404 can be similar to the first plate 402, only the differences between the first plate 402 and the second plate 404 will be discussed in great detail herein, and the same reference numerals will be used to denote the same or similar components. The second plate 404 can have a proximal end 420, a distal end 422, the first side 112 and the second side 114. The second plate 404 can be composed of a suitable biocompatible material, such as a biocompatible metal or polymer. For example, the second plate 404 could be composed of titanium or stainless steel. The second plate 404 can include the plurality of throughbores 26, which can enable the receipt of one or more fasteners, such as a bone fastener, to couple the second plate 404 to the anatomy.

The proximal end 420 of the second plate 404 can include a third bore 424 and a fourth bore 426. Each of the third bore 424 and the fourth bore 426 can be defined through the second plate 404 from the first side 112 to the second side 114. The third bore 424 can be annular or spherical, and can receive a portion of the compression system 406 therethrough. The third bore 424 can include a plurality of threads 424a, which can fixedly couple a portion of the compression system 406 to the third bore 424. The fourth bore 426 can comprise a slot, which can enable the compression system 406 to be coupled to the anatomy at various orientations. The fourth bore 426 can comprise a plurality of teeth or partial threads 426a, which can assist in fixedly coupling or locking a portion of the compression system 406 to the second plate 404. Alternatively, the fourth bore 426 can comprise a smooth circular bore.

The distal end 422 can be curved and shaped to conform to the distal humerus H. The distal end 422 can include the leading portion 116 and a curved portion 428. The curved portion 428 can be shaped to fit around the medial epicondyle 38 of the distal humerus H. The shape of the distal end 422 can cooperate with the compression system 406 to enable the second plate 404 to compress the distal humerus H. The curved portion 428 can include a second compression bore 430. The second compression bore 430 can receive a portion of the compression system 406 to assist in compressing a fracture of the distal humerus H. The second compression bore 430 can include a plurality of threads 430a, which can threadably engage a portion of the compression device 406 to fixedly couple or lock the portion of the compression device 406 to the second plate 404.

With reference to FIGS. 10 and 11, the compression system 406 can cooperate with the first plate 402 and the second plate 404 to compress the fracture of the distal humerus H. The compression system 406 can include a first bone fastener 432, a second bone fastener 434 and a third bone fastener 436. The first bone fastener 432 and the second bone fastener 434 can be longer than the third bone fastener 436 to span a substantially diagonal distance between the first plate 402 and the second plate 404. Each of the first bone fastener 432 and the second bone fastener 434 can include a head 438 and a shank 440. The head 438 can include a plurality of threads 438a, which can assist in coupling the first bone fastener 432 and the second bone fastener 434 to a respective one of the first plate 402 and the second plate 404. The shank 440 can be generally smooth, and can include a plurality of threads 440a at a distalmost end 440b. The plurality of threads 440a can assist in coupling the first bone fastener 432 and the second bone fastener 434 to a respective one of the first plate 402 and second plate 404.

In this regard, the first bone fastener 432 can be inserted through the first compression bore 418 of the first plate 402 to the fourth bore 426 of the second plate 404. The plurality of threads 438a of the head 438 of the first bone fastener 432 can threadably engage the plurality of threads 418a of the first compression bore 418, and the plurality of threads 440a of the shank 440 can be threadably coupled to the plurality of partial threads 426a of the fourth bore 426. The second bone fastener 434 can be inserted through the second compression bore 430 of the second plate 404 to the first bore 412 of the first plate 402. The plurality of threads 438a of the head 438 of the second bone fastener 434 can threadably engage the plurality of threads 430a of the second compression bore 430, and the plurality of threads 440a of the shank 440 can be threadably coupled to the plurality of partial threads 412a of the first bore 412.

The third bone fastener 436 can be smaller than the first bone fastener 432 and the second bone fastener 434. The third bone fastener 436 can include a head 442 and a shank 444. The head 442 can include a plurality of threads 442a for fixedly coupling the third bone fastener 436 to the second plate 404. The head 442 can be generally spherical, but could have any suitable shape. The shank 444 can extend from the head 442. The shank 444 can include a plurality of threads 444a at a distalmost end 444b. The plurality of threads 444a can assist in coupling the third bone fastener 436 to the first plate 402.

In this regard, the third bone fastener 436 can be inserted through the third bore 424 of the second plate 404 to the second bore 414 of the first plate 402. The plurality of threads 442a of the head 442 of the third bone fastener 436 can threadably engage the plurality of threads 424a of the third bore 424, and the plurality of threads 444a of the shank 444 can be threadably coupled to the plurality of partial threads 414a of the second bore 414.

In order to couple the compressive plating system 400 to an anatomy, such as the distal humerus H, an incision can be made adjacent to the distal humerus H. In one exemplary method, with reference to FIG. 1, the first plate 402 can be positioned adjacent to the distal humerus, such that the curved portion 416 is adjacent to the lateral epicondyle 50. One or more bone fasteners can be inserted through the one or more throughbores 26 of the first plate 402 to couple the first plate 402 to the anatomy. The second plate 404 can be positioned opposite the first plate 402 such that the curved portion 428 is adjacent to the medial epicondyle 38. One or more bone fasteners can be inserted through the one or more throughbores 26 of the second plate 404 to couple the second plate 404 to the anatomy.

With or without the use of a guide wire, with reference to FIG. 11, a first bore B5 can be formed through the distal humerus H from the first compression bore 418 of the first plate 402 to the fourth bore 426 of the second plate 404. Then, with or without the use of a guide wire, a second bore B6 can be formed through the second compression bore 430 of the second plate 404 to the first bore 412 of the first plate 402. With or without the use of a guide wire, a third bore B7 can be formed through the distal humerus H from the third bore 424 of the second plate 404 to the second bore 414 of the first plate 402.

Next, in one exemplary method, the first bone fastener 432 can be inserted into the first bore B5 so that the plurality of threads 438a of the head 438 can threadably engage the plurality of threads 418a of the first compression bore 418, and the plurality of threads 440a of the shank 440 can be threadably coupled to the plurality of partial threads 426a of the fourth bore 426. The second bone fastener 434 can be inserted into the second bore B6 so that the plurality of threads 438a of the head 438 can threadably engage the plurality of threads 430a of the second compression bore 430. The plurality of threads 440a of the shank 440 can be threadably coupled to the plurality of partial threads 412a of the first bore 412. The third bone fastener 436 can be inserted into the third bore B7 so that the plurality of threads 442a of the head 442 can threadably engage the plurality of threads 424a of the third bore 424. The plurality of threads 444a of the shank 444 can be threadably coupled to the plurality of partial threads 414a of the second bore 414. It should be noted that the first bore B5, second bore B6 and third bore B7 need not be formed through the anatomy prior to insertion of the first bone fastener 432, second bone fastener 434 and third bone fastener 436, but rather, the first bone fastener 432, second bone fastener 434 and third bone fastener 436 could be driven through the anatomy to form the bores B5-B7.

The insertion and coupling of the first bone fastener 432, second bone fastener 434 and the third bone fastener 436 to the first plate 402 and the second plate 404 can compress a fracture of the distal humerus H. The use of the first bone fastener 432, second bone fastener 434, the third bone fastener 436, first plate 402 and second plate 404 can provide support for two of the three sides of the distal humerus H for stability. The compression system 406 can create compression across the third side of the distal humerus H to provide additional stability for the distal humerus H.

Accordingly, the compression plating system 10, 100, 150, 200, 250, 300, 400 can be used to repair damaged tissue in the anatomy, such as repairing a fracture of the distal humerus H. The compression system 16, 106, 206, 306, 406 can provide compression against the fracture, which can stimulate bone growth and healing. Thus, the use of the compression plating system 10, 100, 150, 200, 250, 300, 400 can improve the recovery time for a patient with a fracture of the distal humerus. In addition, as the compression system 16, 106, 206, 306, 406 can be used with first plates 10, 102, 202, 404 and second plates 14, 104, 254, 406 that are about 180 degrees apart about the distal humerus H and the compression system 16, 206 can be used with first plates 102, 202 and second plates 154, 204 that are about 90 degrees apart about the distal humerus H, the surgeon can be provided with a variety of options to suit the needs of various patients.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A system for compressing a fracture, the system comprising:
    a first bone plate having a first proximal end and a first distal end;
    a second bone plate having a second proximal end and a second distal end;
    a compression system including a first member and a second member;
    the first member coupled to one of the first bone plate and the second bone plate, the first member having a first shank with a threadless portion and having a threaded bore in the threadless portion transverse to an axis of the first member such that the bore is formed substantially perpendicular to a longitudinal axis of the first member; and
    the second member coupled to the other of the first bone plate and the second bone plate such that the second member passes through the bore of the first member, and is threadably coupled to the first member substantially perpendicularly to a longitudinal axis of the first shank such that movement of the first member relative to the second member causes a compressive force to be applied between the first bone plate and the second bone plate.

2. The system of claim 1, wherein the first bone plate comprises a first bore at the first distal end that has a first plurality of threads, and the second bone plate comprises a second bore at the second distal end that includes a second plurality of threads.

3. The system of claim 2, wherein the second member includes a second head and a second shank, the second head having a third plurality of threads and the second shank having a fourth plurality of threads, the third plurality of threads of the second head threadably engagable with the second plurality of threads to couple the second member to the second bone plate.

4. The system of claim 3, wherein the first member includes a first head, the first head having a fifth plurality of threads and the bore in the first shank defining a sixth plurality of threads, the fifth plurality of threads of the first head threadably engagable with the first plurality of threads to couple the first member to the first bone plate.

5. The system of claim 4, wherein the fourth plurality of threads of the second shank are threadably couplable to the sixth plurality of threads of the cross bore to couple the first member to the second member and compress the fracture.

* * * * *